United States Patent
Fink et al.

(10) Patent No.: US 11,134,869 B2
(45) Date of Patent: Oct. 5, 2021

(54) SENSOR DEVICE FOR DETERMINING THE CONCENTRATION OF AN ANALYTE UNDER IN-VIVO CONDITIONS AND PROCESS OF MANUFACTURING

(71) Applicant: Roche Diabetes Care, Inc., Indianapolis, IN (US)

(72) Inventors: Herbert Fink, Mannheim (DE); Bernd Hiller, Mannheim (DE); Ulrich Mueller, Mannheim (DE); Markus Siebenhaar, Penzberg (DE); Christoph Grulke, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 203 days.

(21) Appl. No.: 16/429,996

(22) Filed: Jun. 3, 2019

(65) Prior Publication Data
US 2019/0282142 A1 Sep. 19, 2019

Related U.S. Application Data

(63) Continuation of application No. PCT/EP2017/082039, filed on Dec. 8, 2017.

(30) Foreign Application Priority Data

Dec. 8, 2016 (EP) .................... 16202960

(51) Int. Cl.
*A61B 5/145* (2006.01)
*A61B 5/1486* (2006.01)
*C12Q 1/00* (2006.01)

(52) U.S. Cl.
CPC ...... *A61B 5/14532* (2013.01); *A61B 5/14865* (2013.01); *C12Q 1/002* (2013.01); *C12Q 1/006* (2013.01); *A61B 2562/125* (2013.01)

(58) Field of Classification Search
None
See application file for complete search history.

(56) References Cited

U.S. PATENT DOCUMENTS

| 5,413,690 A | 5/1995 | Kost et al. |
| 5,762,770 A | 6/1998 | Pritchard et al. |
| (Continued) | | |

FOREIGN PATENT DOCUMENTS

| CN | 1623979 A | 6/2005 |
| EP | 2 385 075 A1 | 11/2011 |
| (Continued) | | |

OTHER PUBLICATIONS

G. Verstraete et al., Hydrophilic thermoplastic polyurethanes for the manufacturing of highly dosed oral sustained release matrices via hot melt extrusion and injection molding, International Journal of Pharmaceutics, vol. 506, pp. 214-221, Apr. 22, 2016.
(Continued)

*Primary Examiner* — Thaddeus B Cox
*Assistant Examiner* — Tyra Faith Bookhart
(74) *Attorney, Agent, or Firm* — Bose McKinney & Evans LLP

(57) ABSTRACT

A sensor device for determining the concentration of an analyte under in-vivo conditions that includes an electrode system having an electrode with immobilized enzyme molecules and a diffusion barrier that controls diffusion from the exterior of the electrode system to the immobilized enzyme molecules. The diffusion barrier may include an aliphatic polyurethane. A process of manufacturing such a sensor device is also disclosed.

19 Claims, 10 Drawing Sheets

(56) References Cited

U.S. PATENT DOCUMENTS

| | | | |
|---|---|---|---|
| 5,798,031 A | 8/1998 | Charlton et al. | |
| 5,997,817 A | 12/1999 | Crismore et al. | |
| 6,360,888 B1 | 3/2002 | McIvor et al. | |
| 2003/0100822 A1* | 5/2003 | Lew | A61B 5/14539 600/365 |
| 2008/0242962 A1 | 10/2008 | Roesicke et al. | |
| 2009/0020502 A1 | 1/2009 | Bhullar et al. | |
| 2009/0156920 A1 | 6/2009 | Kotzan et al. | |
| 2013/0126349 A1* | 5/2013 | Zhang | G01N 27/3271 204/403.12 |
| 2013/0245412 A1* | 9/2013 | Rong | A61B 5/14865 600/347 |
| 2014/0018653 A1* | 1/2014 | Staib | C12Q 1/002 600/347 |
| 2014/0128704 A1 | 5/2014 | Simpson et al. | |
| 2014/0275897 A1* | 9/2014 | Pushpala | A61B 5/14503 600/347 |

FOREIGN PATENT DOCUMENTS

| | | |
|---|---|---|
| WO | WO 2007/071562 A1 | 6/2007 |
| WO | WO 2007/147475 A1 | 12/2007 |
| WO | WO 2009/056299 A1 | 5/2009 |
| WO | WO 2010/028708 A1 | 3/2010 |
| WO | WO 2010/130833 A1 | 11/2010 |
| WO | WO 2012/130841 A1 | 10/2012 |
| WO | WO 2013/144255 A1 | 10/2013 |
| WO | WO 2014/001382 A1 | 1/2014 |

OTHER PUBLICATIONS

G. Verstraete et al., Thermoplastic polyurethane-based intravaginal rings for prophylaxis and treatment of (recurrent) bacterial vaginosis, International Journal of Pharmaceutics, vol. 529, pp. 218-226, Jun. 27, 2017.

International Seach Report and Written Opinion of the International Searching Authority, PCT/EP201 7/082039, dated Jan. 26, 2018, 15 pages.

Setti, et. al., An HRP-Based Amperometric Biosensor Fabricated by Thermal Inkjet Printing, Sensors and Actuators B: Chemical, 2007, 6 pages.

* cited by examiner

SENSOR DEVICE FOR DETERMINING THE CONCENTRATION OF AN ANALYTE UNDER IN-VIVO CONDITIONS AND PROCESS OF MANUFACTURING

RELATED APPLICATIONS

This application is a continuation of PCT/EP2017/082039, filed Dec. 8, 2017, which claims priority to EP 16 202 960.7, filed Dec. 8, 2016, the entire disclosures of each of which are hereby incorporated herein by reference.

BACKGROUND

The present disclosure relates to a sensor device for determining the concentration of an analyte under in-vivo conditions and a process of manufacturing. Such sensor devices, which in some cases may also be referred to as implantable biosensors and may be used for determining physiologically relevant analyte concentrations under in-vivo conditions, are generally equipped with an electrode system having an electrode with immobilized enzyme molecules and a diffusion barrier that controls diffusion from the exterior of the electrode system to the immobilized enzyme molecules. The diffusion barrier may be provided with a membrane permeable to the analyte.

The sensor devices are used for the qualitative and/or quantitative analysis of ingredients in biological liquids such as, for example, blood, plasma, ISF or urine. One of the most important analytes is glucose. Examples of other analytes are lactate, PTT, pH, urea, lipids, ethanol, cholesterol and others. Examples of the implementation of electrochemical glucose tests are disclosed in U.S. Pat. Nos. 5,413,690, 5,762,770, 5,798,031, 5,997,817, U.S. Publication No. 2009/0020502 and WO 2009/056299.

Along with so-called point measurements in which a sample of a body fluid is specifically taken from a user and investigated for the analyte concentration, continuous measurements are increasingly becoming available. Continuous glucose measurement in the interstitium, also referred to as continuous monitoring or CM for short, has in the more recent past increasingly attracted attention and recognition as an important method for management, monitoring and control of a diabetes status, for example. Directly implanted electrochemical sensors are usually now used, which are frequently also designated as needle type sensors (NTS). In this case the active sensor region is brought directly to the measurement site, usually located in the interstitial tissue, and for example, using an enzyme, for example glucose oxidase, glucose is converted into electrical current which is related to the glucose concentration and can be used as a measured variable. Examples of such transcutaneous measurement systems are described in U.S. Pat. No. 6,360,888 B1, U.S. Publication No. 2008/0242962 A1 and in WO 2007/071562 A1.

Implantable electrochemical sensors usually have at least two or three electrodes. These are a substance-specific working electrode, a counter electrode and a reference electrode. The counter electrode can serve as a combi-electrode and also as reference. The substance-specific working electrode may be produced by applying an electrically conductive paste containing an enzyme, a mediator and a polymeric binder, to an electrical conductor path. For example, carbon pastes with manganese dioxide ($MnO_2$) and glucose oxidase (GOD) are commonly used. Examples of this are given in WO 2010/130833. Application is accomplished, for example, by means of a flat nozzle coating, by dispensing or by a printing process such as screen printing or ink jet (cf. Setti, et. al., Sensors and Actuators B 126 (2007) 252-257).

The working electrode may be produced by a printing process, e.g., screen or porous printing. The material base of the working electrode may comprise a screen printing paste which must be electrically conductive (carbon pastes) and to which detection-specific components are added. These may be $MnO_2$, enzyme and other conductive carbon modifications. Conventional screen printing (carbon) pastes are optimized in relation to the composition of their components so that they meet the high requirements of the screen printing technique. In order to obtain the screen printing material for a functional working electrode from these pastes, further components are added to the screen printing paste. Such components may comprise at least one of enzyme (GOD) (e.g., about 0.5 to 5 weight %), water (e.g., about 2 to 8 weight %), $MnO_2$ (e.g., about 12 to 20 weight %), and dispersing agent (e.g., about 5 to 15 weight %). It leads to substantial change of the nature of the original paste.

The diffusion barrier of the sensor device has to satisfy different requirements. Since, in the case of sensors devoid of such a barrier, it is not generally possible to measure the entire physiologically relevant concentration range, it has the task of reducing the diffusive material transport of the analyte to the sensor electrodes and thus of extending the measurement range of the sensor. The local consumption of the analyte in the vicinity of the electrode system, which is obligatory when taking the measurement, is reduced by this property. This is advantageous inasmuch as the analyte consumption of the sensor system falsifies the in-vivo concentration at the location of the sensor electrodes. The diffusion barrier thus contributes to the correctness of the measurement result. For the in in-vivo use of biosensors, it is even more important however for the diffusion barrier to prevent elution of soluble, and possibly toxic, (bio) components of the sensor into the patient body.

In addition, it is desirable for the membrane of the diffusion barrier itself to be biocompatible and for proteins of the immune system not to adhere to the membrane, block it, or diffuse through it (prevention of "sensor poisoning"). Furthermore, it is advantageous if the diffusion barrier additionally keeps endogenous or exogenous interferents away from the sensor electrodes.

A sensor device for determining the concentration of an analyte under in-vivo conditions is known from WO 2010/028708 A1. Another example of such sensor device is disclosed in WO 2012/130841 A1.

WO 2007/147475 A1 discloses an amperometic sensor configured for implantation into a living body to measure the concentration of an analyte in a body fluid. An alternative sensor element is disclosed in WO 2014/001382 A1.

SUMMARY

This disclosure provides improved technology for a sensor device for determining the concentration of an analyte under in-vivo conditions, especially for determining the concentration of an analyte in a bodily fluid.

A sensor device for determining the concentration of an analyte under in-vivo conditions is disclosed. The device comprises an electrode system having an electrode with immobilized enzyme molecules and a diffusion barrier that controls diffusion from the exterior of the electrode system to the immobilized enzyme molecules. The diffusion barrier comprises an aliphatic polyurethane.

The device may be provided for determining the concentration of an analyte in a bodily fluid, e.g., the concentration of blood glucose.

The diffusion barrier may be made of the aliphatic polyurethane.

The diffusion barrier may be provided with a molecular weight cut off (MWCO) of <10 kDa.

The diffusion barrier may be provided as a membrane covering at least the electrode with the immobilized enzyme molecules. The electrode covered with the immobilized enzyme molecules may also be referred to as a working electrode.

In another embodiment, the diffusion barrier may be provided with a water absorption capacity of at least 20 percent of its own weight.

The diffusion barrier can be made of a material comprising:

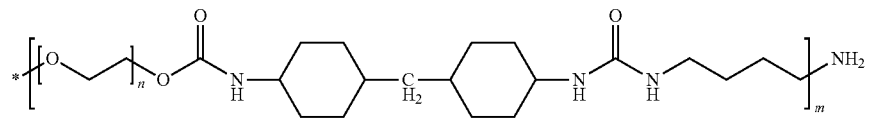

A glucose sensor device may be provided, wherein membrane-immobilized enzyme molecules are selected for determining a glucose concentration in a bodily fluid, such as blood.

The glucose sensor may be configured for determining the concentration of the glucose level, which in turn is indicative of the blood glucose level, and wherein the concentration may be determined in a range of concentration from about 20 to about 800 mg/l, alternatively in a range from about 40 to about 500 mg/l.

The diffusion barrier may be provided by a layer having a layer thickness of about 5 to about 50 μm, and, more particularly, from about 15 to about 30 μm.

The diffusion barrier may be provided by a cover layer covering at least partially an electrode path. The cover layer may fully or partially cover an enzyme layer containing the immobilized enzyme molecules.

With regard to the process of manufacturing, the tempering step may be performed at a temperature of 30° C.-60° C., preferably at 35° C.-50° C., more preferably at a temperature 38° C.-45° C., or much more preferably at a temperature of about 40° C.

The tempering step may be performed for 12-150 hours, preferably 24-120 hours, or even more preferred 48-60 hours.

The tempering step may be performed at 30° C.-60° C., preferably at 35° C.-50° C., more preferably at a temperature of 38° C.-45° C., or much more preferably at a temperature of about 40° C., and for 12-150 hours, preferably 24-120 hours, or, very much preferred 48-60 hours. In one particular embodiment, the tempering may be performed at a temperature of about 40° C. for a period of 48 to 60 hours.

The sensor device may have a sensitivity loss over a storage period of less than 20%, preferably less than 15% over a period of 3 months, and/or less than 20% over a period of 1 year.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
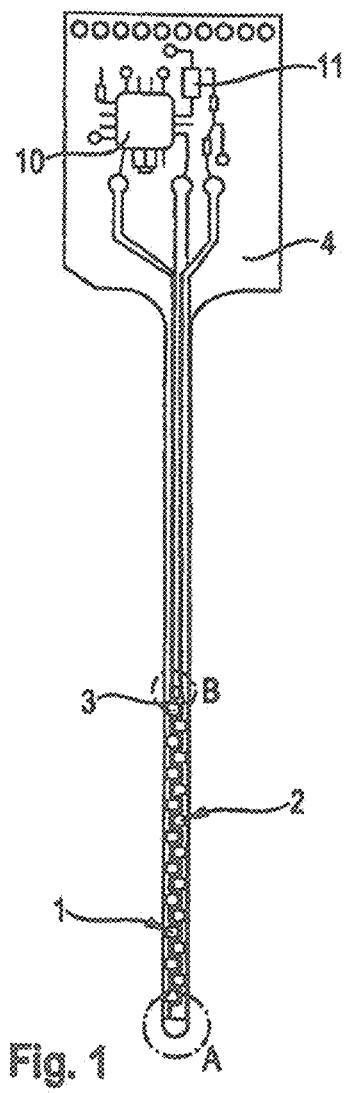
FIG. 1 is a schematic representation of an exemplary embodiment of an electrode system.
Figure 2:
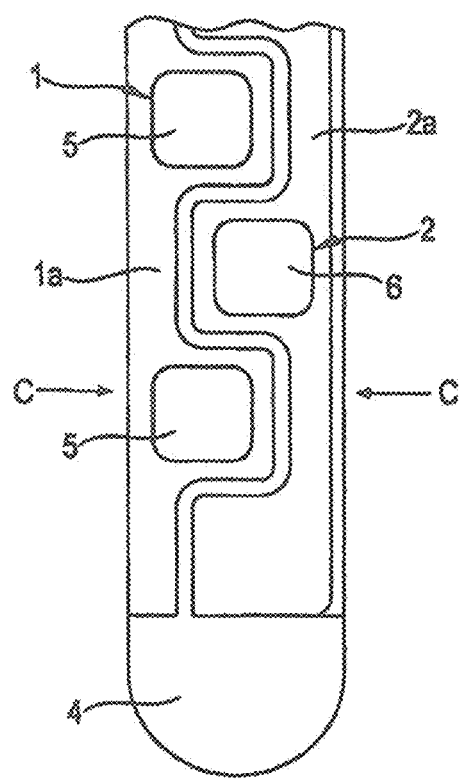
FIG. 2 is an enlarged detail view of the area designated "A" in FIG. 1.
Figure 3:
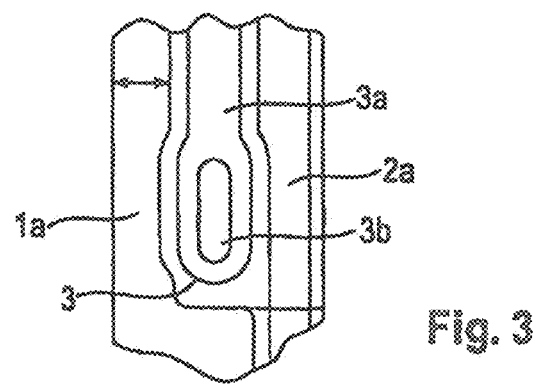
FIG. 3 is an enlarged detail view of the area designated "B" in FIG. 1.
Figure 4:
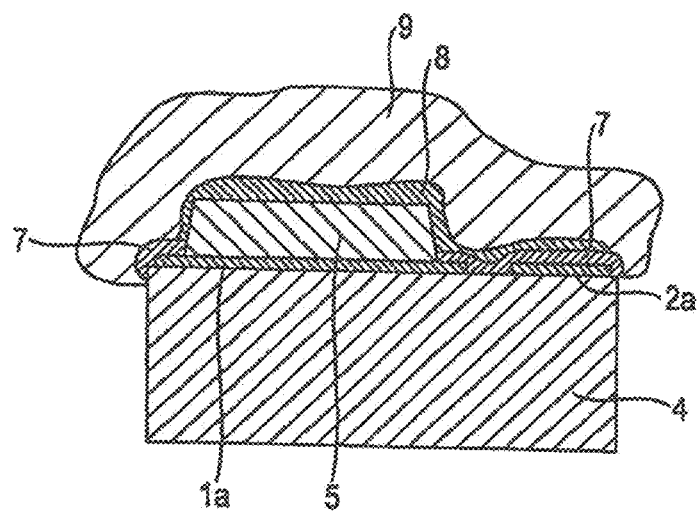
FIG. 4 is a section along the section line C-C of FIG. 2.

FIG. 1 shows an exemplary embodiment of a sensor device (electrode system) for insertion into body tissue of a human or animal, for example into cutis or subcutaneous fatty tissue. A magnification of detail view A is shown in FIG. 2, a magnification of detail view B is shown in FIG. 3. FIG. 4 shows a corresponding sectional view along the section line, C-C, of FIG. 2.

The electrode system shown has a working electrode 1, a counter electrode 2, and a reference electrode 3. Electrical conductors 1*a*, 2*a*, 3*a* of the electrodes 1, 2, 3 are arranged in the form of metallic conductor paths, preferably made of palladium or gold, on a substrate 4. In the exemplary embodiment shown, the substrate 4 is a flexible plastic plate, for example made of polyester. The substrate 4 is less than 0.5 mm thick, for example 100 to 300 micrometers, and is therefore easy to bend such that it can adapt to movements of surrounding body tissue after its insertion. The substrate 4 has a narrow shaft for insertion into body tissue of a patient and a wide head for connection to an electronic system that is arranged outside the body. The shaft of the substrate 4 preferably is at least 1 cm in length, in particular 2 cm to 5 cm.

In the exemplary embodiment shown, the sensor device is at least partially implantable into a body tissue. With regard to the sensor device shown, part of the measuring facility, namely the head of the substrate 4, may project from the body of a patient during use. In alternative sensor devices, it is feasible to implant the entire measuring facility and transmit measuring data in a wireless fashion to a receiver that is arranged outside the body.

The working electrode 1 carries an enzyme layer 5 that contains immobilized enzyme molecules for catalytic conversion of the analyte. The enzyme layer can be applied, for example, in the form of a curing paste of carbon particles, a polymeric binding agent, a redox mediator or an electrocatalyst, and enzyme molecules. Details of the production of an enzyme layer 5 of this type are disclosed, for example, in WO 2007/147475 A1, the entire disclosure of which is hereby incorporated herein by reference.

In an alternative embodiment, a composition comprising carbon paste mixed with manganese dioxide ($MnO_2$) may be prepared and applied to the working electrode 1. The composition may be prepared as a paste. Following, an enzyme layer may be applied for preparing the enzyme layer 5 containing the immobilized enzyme molecules for catalytic conversion of the analyte.

In the exemplary embodiment shown, the enzyme layer 5 is not applied continuously on the conductor 1a of the working electrode 1, but rather in the form of individual fields that are arranged at a distance from each other. The individual fields of the enzyme layer 5 in the exemplary embodiment shown are arranged in a series.

The conductor 1a of the working electrode 1 has narrow sites between the enzyme layer fields that are seen particularly well in FIG. 2. The conductor 2a of the counter electrode 2 has a contour that follows the course of the conductor 1a of the working electrode 1. This means results in an intercalating or interdigitated arrangement of working electrode 1 and counter electrode 2 with advantageously short current paths and low current density.

In order to increase its effective surface, the counter electrode 2 can be provided with a porous electrically conductive layer 6 that is situated in the form of individual fields on the conductor 2a of the counter electrode 2. Like the enzyme layer 5 of the working electrode 1, this layer 6 can be applied in the form of a curing paste of carbon particles. In an alternative embodiment, the paste may comprise a polymeric binding agent.

The fields of the layer 6 preferably have the same dimensions as the fields of the enzyme layer 5, although this is not obligatory. However, measures for increasing the surface of the counter electrode can just as well be foregone and the counter electrode 2 can just as well be designed to be a linear conductor path with no coatings of any kind, or with a coating made from the block copolymer and optionally a spacer.

The reference electrode 3 is arranged between the conductor 1a of the working electrode 1 and the conductor 2a of the counter electrode 2. The reference electrode 3 shown in FIG. 3 consists of a conductor 3a on which a field 3b of conductive silver/silver chloride paste is arranged.

FIG. 4 shows a schematic sectional view along the section line, C-C, of FIG. 2. The section line, C-C, extends through one of the enzyme layer fields 5 of the working electrode 1 and between the fields of the conductive layer 6 of the counter electrode 2. Between the fields of enzyme layer 5, the conductor 1a of the working electrode 1 can be covered with an electrically insulating layer 7, like the conductor 2a of the counter electrode 2 between the fields of the conductive layers 6, in order to prevent interfering reactions which may otherwise be catalyzed by the metal of the conductor paths 1a, 2a. The fields of the enzyme layer 5 are therefore situated in openings of the insulation layer 7. Likewise, the fields of the conductive layer 6 of the counter electrode 2 may also be placed on top of openings of the insulation layer 7.

The enzyme layer 5 is covered by a cover layer 8 which presents a diffusion resistance to the analyte to be measured and therefore acts as a diffusion barrier. The cover layer 8 consists of an aliphatic polyurethane (see FIG. 5).

A favorable thickness of the cover layer 8 is, for example, about 5 to about 50 µm, particularly from about 15 to about 30 µm. Such thickness of the cover layer 8 may provide for configuring the glucose sensor for determining the concentration of blood glucose in a range of concentration from about 20 to about 800 mg/l, alternatively in a range from about 40 to about 500 mg/l.

Because of its diffusion resistance, the cover layer 8 (diffusion barrier) may cause fewer analyte molecules to reach the enzyme layer 5 per unit of time. Accordingly, the cover layer 8 may reduce the rate at which analyte molecules are converted, and therefore counteracts a depletion of the analyte concentration in surroundings of the working electrode. More particularly, the diffusion layer slows down the transport of glucose to the active layer, thereby stabilizing the local glucose concentration at a level comparable to that found in the circulation.

The cover layer 8 forming the diffusion barrier extends continuously essentially over the entire area of the conductor 1a of the working electrode 1. A biocompatible layer 9 is arranged on the cover layer 8. For other embodiments, the biocompatible layer 9 may not be present.

In an embodiment the biocompatible layer 9 may provide for a spacer that is an additional layer optionally provided and may establish a distance between the enzyme layer 5 and cells of surrounding body tissue.

The biocompatible layer 9 may be made from a copolymer of (meth) acrylates or may be made of a methacrylate-based polymer. In an embodiment, the biocompatible layer 9 is a copolymer from at least 2 or 3 (meth)acrylates. The biocompatible layer 9 may be highly permeable for the analyte, i.e., it does significantly lower the sensitivity per area of the working electrode, for example 20% or less, or 5% or less with a layer thickness of less than about 20 µm, preferably less than about 5 µm. The thickness of the biocompatible layer may be from about 1 to about 3 µm.

The enzyme layer 5 of the electrode system can contain metal oxide particles, preferably manganese dioxide particles, as a catalytic redox mediator. Manganese dioxide catalytically converts hydrogen peroxide that is formed, for example, by enzymatic oxidation of glucose and other bioanalytes. During the degradation of hydrogen peroxide, the manganese di-oxide particles transfer electrons to conductive components of the working electrode 1, for example, to graphite particles in the enzyme layer 5. The catalytic degradation of hydrogen peroxide counteracts any decrease of the oxygen concentration in the enzyme layer 5. Advantageously this allows the conversion of the analyte to be detected in the enzyme layer 5 to not be limited by the local oxygen concentration. The use of the catalytic redox mediator therefore counteracts a falsification of the measuring result by the oxygen concentration being low. Another advantage of a catalytic redox mediator is that it prevents the generation of cell-damaging concentrations of hydrogen peroxide.

The preferred spacer membrane polymer described herein may be used as an outer coating for a diffusion barrier, but also as an outer coating of an electrode system in general, particularly of an electrode system for measuring the concentration of an analyte under in-vivo conditions, comprising an electrode with immobilized enzyme molecules and a diffusion barrier that controls diffusion of the analyte from the exterior of the electrode system to the enzyme molecules.

A sensor device was manufactured as described, for example, in WO 2010/028708 A1, the entire disclosure of which is hereby incorporated herein by reference. However, the manufactured sensor differed from that disclosed in WO 2010/028708 in that the diffusion barrier was provided by a film made of the aliphatic polyurethane of the structure shown in FIG. 5.

In a further embodiment, the diffusion layer according to the present disclosure is provided by a film made of polyurethane, preferably aliphatic polyurethane, that is a multiphase block copolymer comprising soft blocks and hard blocks as basic structural units. These soft blocks and/or hard blocks are obtained by reacting dioles and isocyanates. As used herein, a soft block may be selected from the group comprising polyols or soft blocks prepared from diols as educts. Further, as used herein, a hard block is selected from the group comprising those for which diisocyanate components may be used as educts and may further comprise a chain extender. The diisocyanate component educts may be selected from the group comprising TDi, MDI, IPDI, HMDI, and is preferably HDI or MDI (cf. https://dii.americanchemistry.com/Diisocyanates-Explained/). The chain extender may be selected from the group comprising those prepared from dioles or amines, preferably butadiol, butanamine, methylamine, methylpropylamine, butyldimethylamin, ethylmethylpropylamin, ethandiol, propandiol, dimethylbutandiol, etc.

In a further embodiment, the diffusion layer according to the present disclosure is provided by a film made of aliphatic polyurethanes that are selected from hydrophilic aliphatic thermoplastic polyurethanes of different grades (e.g., HP60D20, HP60D35, HP93A100, SP60D60, SP93A100, SP80A150, TG500, TG2000, Maderuelo et al., 2011, J. Control. Release, 154, 2-19) marketed as Tecophilic™, preferably Tecophilic grade HP60D20, or similar products.

In a further embodiment, the technologies for the diffusion barrier according to the present disclosure may be applied to a sensor type disclosed in WO 2014/001382 A1 to which, with regard to an alternative, reference is as to the sensor device structure. For the sensor disclosed in WO 2014/001382 A1, a membrane covering at least one of the working electrode and the counter electrode may be provided with the diffusion barrier according to the present disclosure. WO 2014/001382 is hereby incorporated herein by reference in its entirety.

Figure 5:
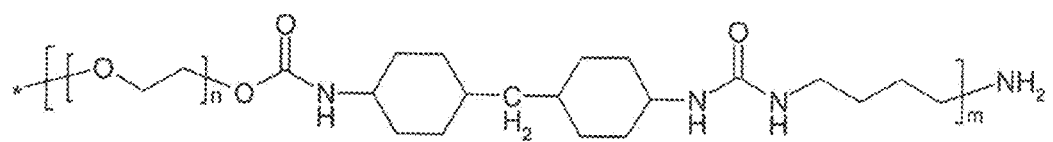
FIG. 5 presents the chemical structure of a barrier membrane material.

For further analyzing the barrier layer permeation measurements were performed for the material shown in FIG. 5. By such permeation measurements the aliphatic polyurethane was experimentally determined to have a MWCO of <10 kDa.

Due to this MWCO, this polymer is particularly suitable as a membrane material for in-vivo sensors, since it is permeable to many physiologically relevant analytes in the size of glucose and lactate, but also blocks the passage of most proteins, both of toxic enzymes which cannot bleed out from the sensor device and pass into the body, and also those proteins of the patient's immune system that could poison the sensor surface.

Analytes that are to pass through the barrier membrane and molecules of which the passage is to be prevented generally differ in terms of their molecule size. Whereas the molecules to be blocked are generally proteins having molecule sizes in the kDa range, the molar masses of the analyte of physiological interest, e.g., glucose or lactate, reside in the sub-kDa range. The differentiation between molecules that are to penetrate the membrane and those of which the passage is to be prevented by the membrane can therefore be implemented via a size exclusion or MWCO.

The MWCO of membranes can be determined in what are known as permeation measurements. During these measurements, the membrane to be examined is mounted in a measuring chamber. Here, the membrane separates the chamber into two compartments, specifically the feed side and the permeate side. A solution that contains one or more substances having defined molecular weights is filled into the feed compartment. A solution devoid of such substances is located on the permeate side. In the ideal case, the solutions on the feed side and permeate side are stirred. After a sufficient residence time in the chambers (a swell time is to be taken into account here, in which the maximum permeability of the membrane is set), it is checked with use of samples from the permeate whether molecules from the feed were able to diffuse through the membrane into the permeate. Provided the membrane discriminates between differently sized molecules, the MWCO of the membrane can be determined on the basis of the molecular weight of the largest molecules that were still able to pass through the membrane.

Many aliphatic polyurethanes have the property of structuring with increasing storage life, whereas aromatic polyurethanes do not, or less pronouncedly so, exhibit this property. This structuring may be described as "kneading of the polymer chains" which occurs even when a respective product is present in a solid aggregate state, e.g., as granules. When the granules are dissolved in a solvent, as in the preparation of an immersion solution for sensor coating, the structuring of the molecules is dissolved. If the sensors are immersed in the immersing solution and a thin coating is applied to the sensor surface, and the solvent is then removed from the coating by drying, the structuring of the molecular chains in the coating begins. A freshly coated sensor, in which the structuring of the molecules in the membrane is not yet advanced, shows a high sensitivity when measured in synthetic glucose solution. This is attributed to the fact that the membrane, which has not yet been completely structured, comparatively blocks the glucose passage. This hypothesis is confirmed by measuring data on the membrane resistance, which can be determined in impedance measurements and which is a measure of the permeability of the membrane. The membrane resistance of freshly made patterns is comparatively low.

It is also noticeable, when measuring in synthetic glucose solution, that a moderate increase in the signal at the beginning of the measurement (drift in the running-in phase, typically described by a drift parameter (D (day2) determined on day 2) is explained by the fact that the membrane, when it comes into contact with the measuring solution, begins to swell and takes up water. With increasing swelling the permeability increases for the passage of the glucose and thus also the sensitivity. The sensor signal is stable only when the membrane has reached its maximum absorption capacity.

Figure 6:
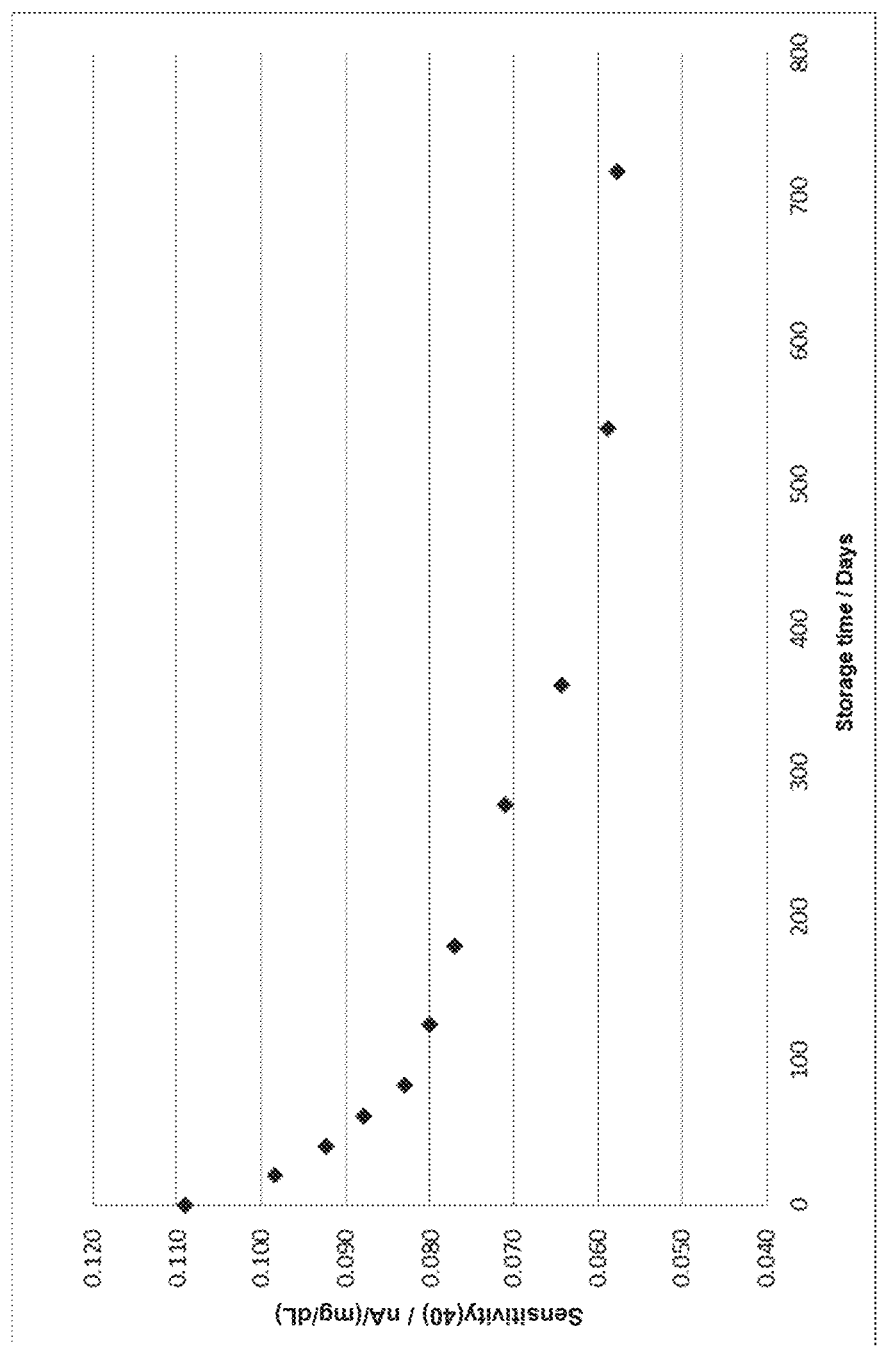
FIG. 6 is a graphical representation of sensor sensitivity over time measured for sensor devices in glucose solution.
Figure 7:
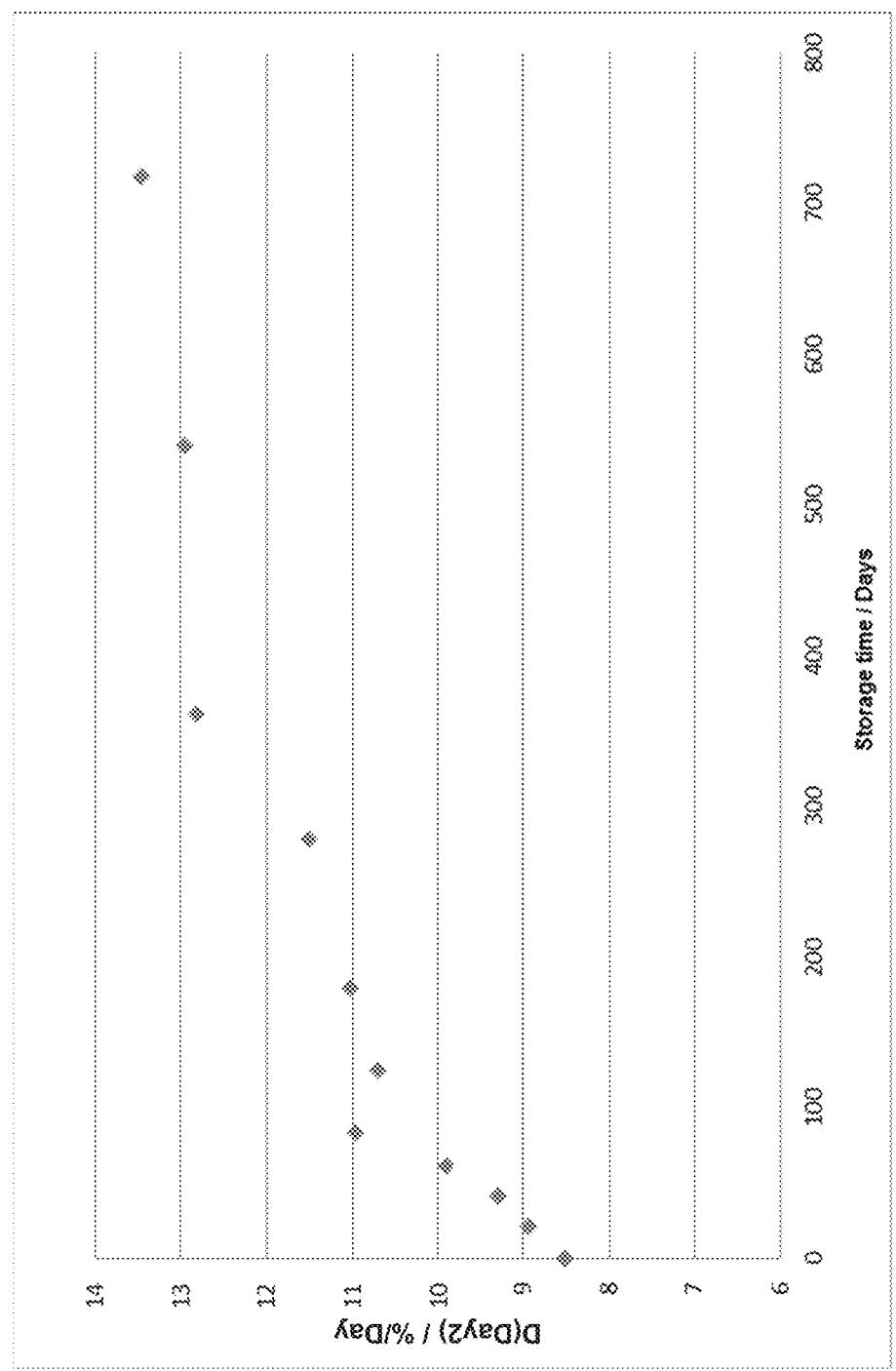
FIG. 7 is a graphical representation of run-in behavior over time for drift parameter D(day2) (determined on day 2) for sensor devices measured for sensor devices in glucose solution.
Figure 8:
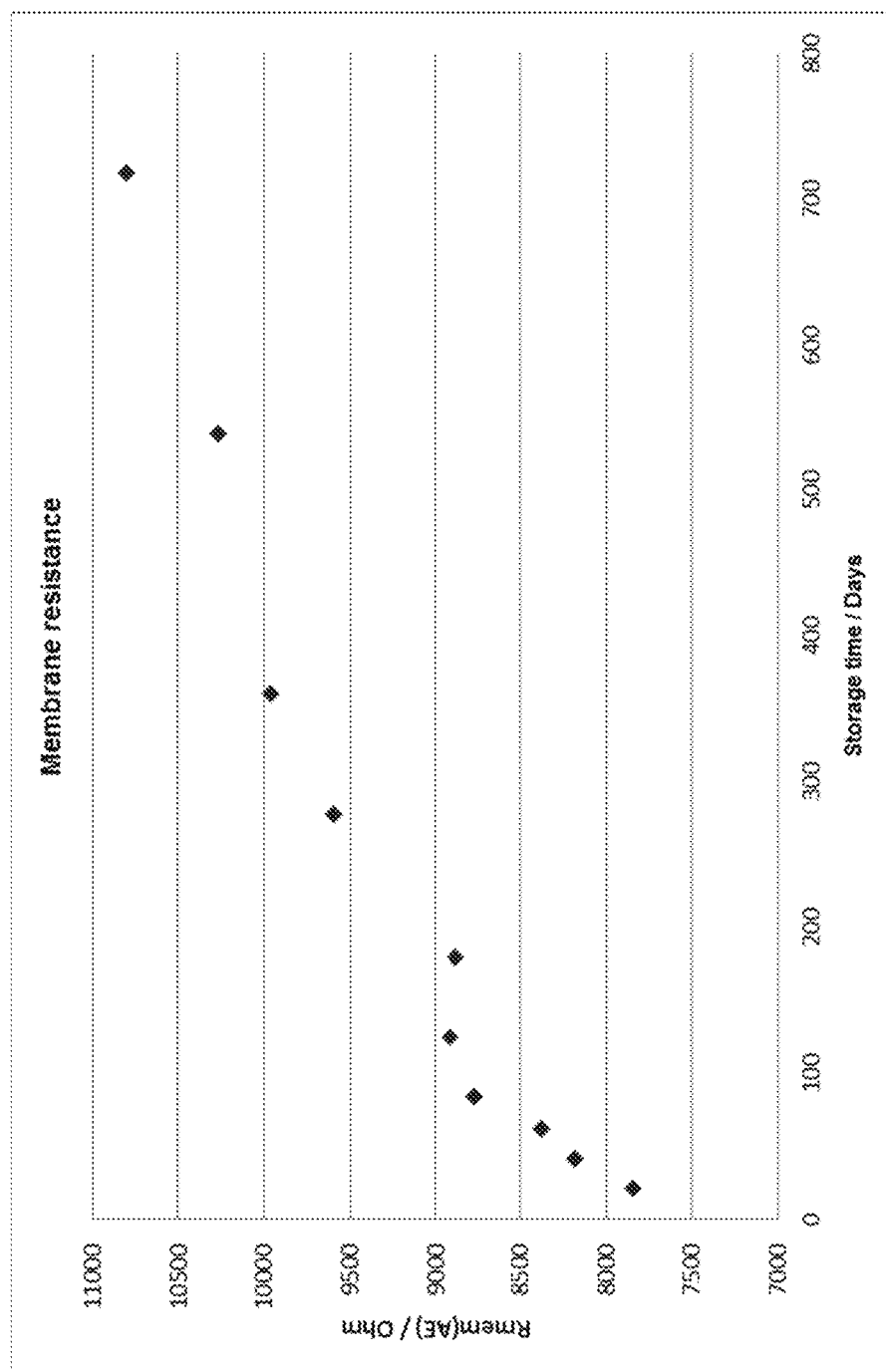
FIG. 8 a graphical representation of membrane resistance over time for sensor devices stored at a temperature of 20-25° C.

If the sensors are coated with aliphatic polyurethanes at room temperature, the structuring of the molecules in the membrane continues as described above. At the same time, longer-stored sensors tend to show a reduced sensitivity when measured in glucose solution (see FIG. 6) and a modified run-in behavior (see FIG. 7). The membrane restructuring in the aliphatic polyurethane and these performance changes in the glucose measurement over the storage time can be shown by means of membrane resistance measurements. Conversely, the membrane resistance tends to increase over the storage time (see FIG. 8). This is inversely proportional to the sensitivity loss and proportional to the drift parameter.

The consequences of the structuring of the aliphatic polyurethane membrane over the storage time, in particular the associated change in the inflow behavior, may present a problem for the mathematical evaluation algorithm, which must convert the sensor current into a concentration. In the sensitivity algorithm, a defined drift over the measurement time is assumed. If the sensitivity course changes due to the restructuring in the membrane, the evaluation algorithm must take this into account. This is currently being solved in such a way that an "average sensitivity trend" is stored in the algorithm which, as a compromise, best describes the sensitivity profile of both fresh and stored sensors.

However, an algorithm which changes with the age of the sensors, or a sensor that changes less or less strongly over the age, would be advantageous. This would not only be advantageous for the accuracy of the measurement result but would also help to reduce the number of necessary calibrations or even allow a "factory calibration." The present disclosure provides a process of manufacturing correspondingly produced sensors that have the above surprising and advantageous effects.

In one embodiment, a process for the manufacturing of the herein described sensors is provided, wherein, by means of special tempering conditions, it has been possible to stabilize the sensitivity profile of aliphatic polyurethane (e.g., Tecophilic HP60D20)-coated sensors in the desired manner. According to the present disclosure, the sensors are re-stored during the tempering under defined temperature conditions after the conventional drying process. In embodiments, 24 to 120-hour tempering at 40 to 60° C. results in the stabilization of not only the sensitivity but also the inflow behavior (see FIGS. 9 and 10).

Figure 9:
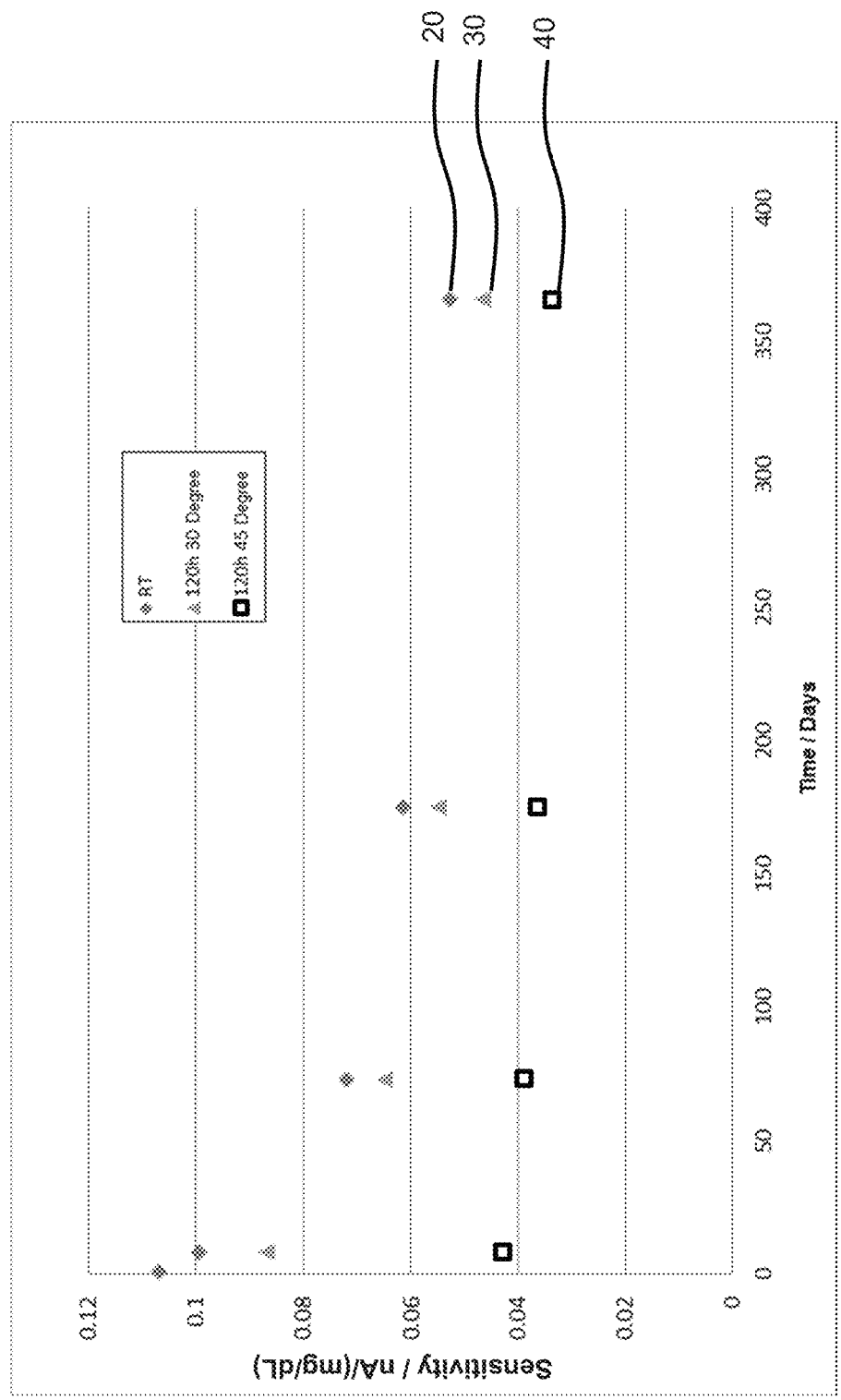
FIG. 9 is a graphical representation of sensor sensitivity over storage time for sensor devices tempered under different conditions.
Figure 10:
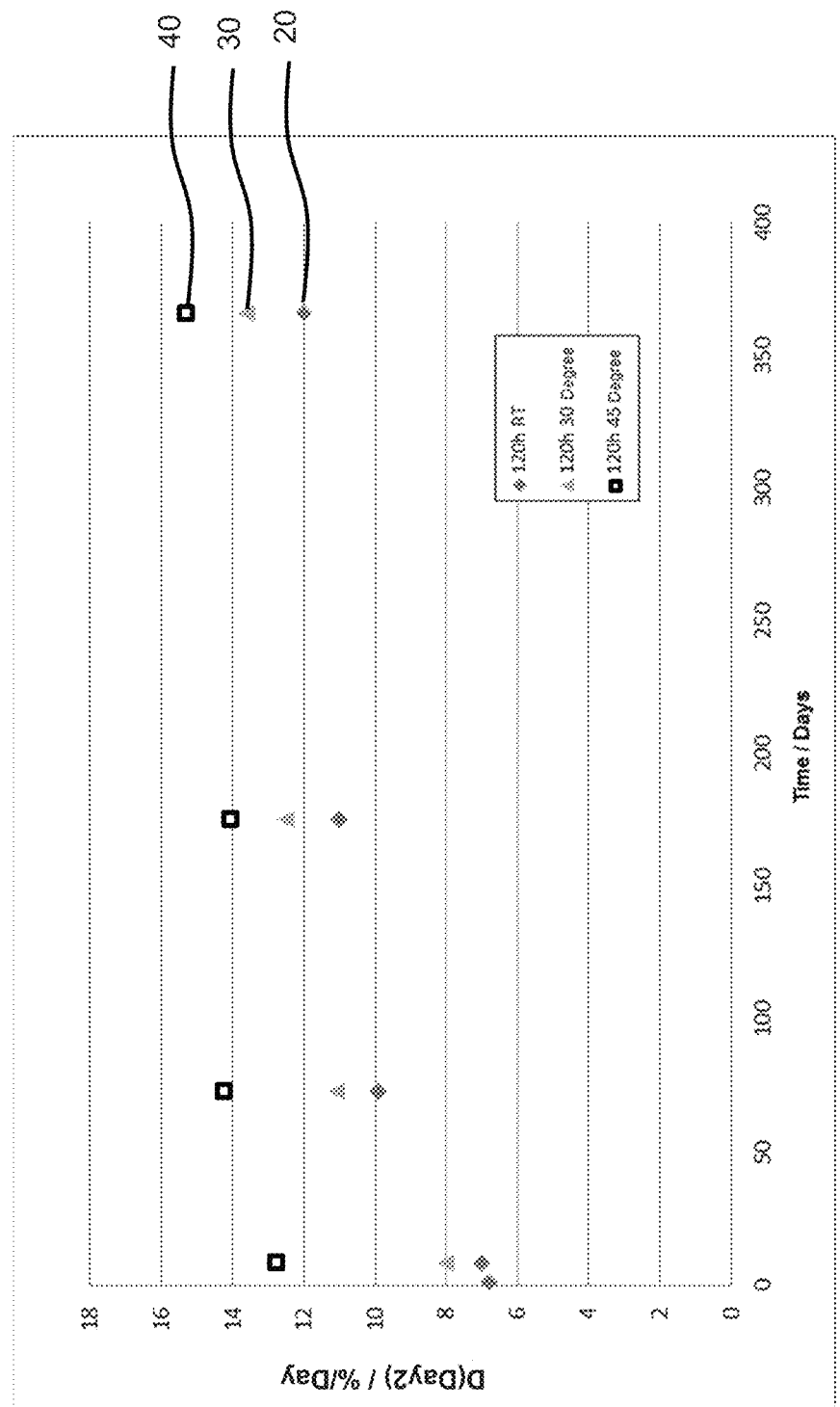
FIG. 10 is a graphical representation of run-in behavior over time for drift parameter D(day2) (determined on day 2) for sensor devices measured for the sensor devices tempered under different conditions.

Referring to FIGS. 9 and 10, graphical points 20 (rhomb) refer to sensor devices not tempered. Graphical points 30 (triangle) refer to sensor devices tempered for 120 hours at a temperature of 30° C. Graphical points 40 (hollow square) refer to sensor devices tempered for 120 hours at a temperature of 45° C.

Although tempering may be at the expense of the signal intensity, which suggests that the sensor components have been damaged, it has been shown by membrane resistance measurements on the tempered sensors that the process according to the present disclosure that the sensitivity loss during tempering is similar to the aging during storage at room temperature due to a change/structuring of the membrane. Thermal stress tests on the enzyme show that the sensitivity loss in the selected annealing conditions has not been caused by enzyme deactivation.

In order to counteract any loss of sensitivity by tempering, the sensor diaphragm can be designed to be thinner than it was previously in the process according to the present disclosure. Accordingly, the sensors according to the present disclosure have a thickness of about 5-50 μm, preferably 15-30 μm without tempering, and tempered sensors preferably have a thickness of about 5-50 μm and preferably about 5-15 μm. As long as the membrane is thick enough to have a defect-free layer on the working electrode, the coating is sufficient to prevent enzyme leakage from the working electrode.

It has also surprisingly been found that the tempering of the sensors forces the restructuring process in the aliphatic polyurethane membrane. The tempering conditions in the process of manufacturing are preferably chosen in such a way that, on the one hand, the tempering process is carried out quickly, cost-effectively and efficiently, and that, on the other hand, other sensor components are not damaged. At a temperature of 30° C., the restructuring tends to be too slow. Sensors that were tempered at this temperature for 120 h showed a still very changing sensor performance for weeks. Surprisingly, it was only at 40° C. that a considerable stabilization could be achieved with a tempering lasting several hours. The temperature should not be above 60° C. Above this limit temperature, a thermal deactivation, and at even higher temperatures, a deformation of the sensor substituent can be expected.

Therefore, the present disclosure relates also to a process of manufacturing a sensor device according to any of the above embodiments, wherein the process includes a tempering step of the sensor.

In further embodiments of the manufacturing process the tempering step is performed at a temperature ≥30° C., preferably at ≥35° C., more preferably at a temperature ≥37° C., ≥38° C., ≥39° C., or even more preferably at a temperature ≥40° C.

In further embodiments of the foregoing manufacturing processes, the process includes a tempering step that is performed for at least 24 hours, more preferably for at least 48 hours, 72 hours, 96 hours or, even more preferably, for at least 120 hours.

In an embodiment, the process of manufacturing according to the disclosure comprises a tempering step that is performed at a temperature of ≥35° C., preferably at a temperature ≥40° C. for at least 96 hours, and preferably for at least 120 hours.

In accordance with the present disclosure, a sensor device corresponding to any of the embodiments of the present disclosure is obtainable or is obtained by a process of manufacturing as describe in the preceding paragraphs.

In accordance with the present disclosure, the various sensor devices and manufacturing processes described herein may include or involve a diffusion layer that is provided by a film made of aliphatic polyurethanes that are selected from hydrophilic aliphatic thermoplastic polyurethanes of different grades (e.g., HP60D20, HP60D35, HP93A100, SP60D60, SP93A100, SP80A150, TG500, TG2000, Maderuelo et al., 2011, J. Control. Release, 154, 2-19) marketed as Tecophilic™, preferably Tecophilic grade HP60D20.

Such a sensor device may have a sensitivity loss over a storage period of less than 20%, preferably less than 15% over a period of 3 months, and/or less than 20% over a period of 1 year.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A sensor for determining a concentration of an analyte under in-vivo conditions, comprising:
   an electrode system having an electrode with immobilized enzyme molecules;
   a diffusion barrier that controls diffusion from an exterior of the electrode system to the immobilized enzyme molecules, wherein the diffusion barrier comprises an aliphatic polyurethane; and
   wherein the sensor has a sensitivity loss of less than 15% over a storage period of 3 months.

2. The sensor according to claim 1, wherein the diffusion barrier only allows passage of molecules having a molecular weight of less than 10 kDa.

3. The sensor according to claim 1, wherein the diffusion barrier includes a membrane covering the electrode with immobilized enzyme molecules.

4. The sensor according to claim 1, wherein the diffusion barrier has a water absorption capacity of less than 50%.

5. The sensor according to claim 4, wherein the diffusion barrier has a water absorption capacity within the range of 20-35%.

6. The sensor according to claim 1, wherein the diffusion barrier includes a hydrophilic aliphatic thermoplastic polyurethane.

7. The sensor according to claim 1, wherein the immobilized enzyme molecules are configured to determine glucose concentration in a bodily fluid.

8. The sensor according to claim 7, wherein the sensor is configured for determining the glucose concentration in a range of concentration from about 20 to about 800 mg/l.

9. The sensor according to claim 1, wherein the diffusion barrier has a layer thickness of about 5 to about 50 μm.

10. The sensor according to claim 1, wherein the diffusion barrier includes a cover layer at least partially covering an electrode path of the electrode system.

11. The sensor according to claim 1, wherein the sensor has a sensitivity loss of less than 20% over a storage period of 1 year.

12. A process of manufacturing a sensor according to claim 1 which includes the step of tempering the sensor.

13. The process according to claim 12, wherein the tempering step is performed at a temperature within the range of 30° C.-60° C.

14. The process according to claim 13, wherein the tempering step is performed at a temperature within the range of 35° C.-50° C.

15. The process according to claim 14, wherein the tempering step is performed at a temperature within the range of 38° C.-45° C.

16. The process according to claim 15, wherein the tempering step is performed at a temperature of about 40° C.

17. The process according to claim 12, wherein the tempering step is performed for a time period within the range of 12-150 hours.

18. The process according to claim 17, wherein the tempering step is performed for a time period within the range of 24-120 hours.

19. The process according to claim 18, wherein the tempering step is performed for a time period within the range of 48-60 hours.

* * * * *